United States Patent [19]

Li

[11] Patent Number: 6,106,830

[45] Date of Patent: Aug. 22, 2000

[54] METHODS FOR THE TREATMENT OF APOPTOSIS-RELATED DISEASES BY BATROXOBIN

[75] Inventor: Qing you Li, Tianjin, China

[73] Assignee: Tobishi Pharmaceutical Co., Ltd., Tokyo, Japan

[21] Appl. No.: 08/911,058

[22] Filed: Aug. 14, 1997

[30] Foreign Application Priority Data

Aug. 29, 1996 [JP] Japan .................................. 8-227953

[51] Int. Cl.⁷ .................................................. A61K 38/48
[52] U.S. Cl. ...................... 424/94.64; 424/542; 530/350; 530/856; 514/2
[58] Field of Search ............................... 424/94.64, 542; 514/2; 530/350, 856

[56] References Cited

U.S. PATENT DOCUMENTS

| 3,849,252 | 11/1974 | Percs et al. | ................................. | 195/62 |
| 5,595,974 | 1/1997 | Tomaru | ..................................... | 514/21 |

FOREIGN PATENT DOCUMENTS

| 0 719 791 | 7/1996 | European Pat. Off. . |
| 0 750 912 | 1/1997 | European Pat. Off. . |
| WO 93/25683 | 12/1993 | WIPO . |
| WO 95/03054 | 2/1995 | WIPO . |

OTHER PUBLICATIONS

Takanashi et al. (CA 104:14790, abstract of Oyo Yakari, (1985), 30 (3), pp. 481–486).

Ozaki et al., (CA 99:169290, abstract of Oyo Yakuri (1983), 26 (1), pp. 55–77).

Tanaka et al., (CA 93: 180638, abstract of Ketsueki to Myakkan (1980), 11 (1), pp. 30–34).

Peigen Kuang et al., (CA96:455640, Source : Third Meeting of the Asian–Pacific Society for Neurochemistry and Fifth Meeting of the Chinese Society for Neurochemistry, Beijing, China, Oct. 8–10, 1996. Journal of Neurochemistry 67 (Suppl.), 1996, S29, ISSN: 0022–3042.

Kuang, P. et al., (AN 97–054438–06, WPIDS, abstract of EP 750912), 1997.

Toulon P. et al., (AN 94:93463, Thirty–fifth Annual Meeting of the American Society of Hematology, St. Louis, Missouri, USA, Dec. 3–7, 1993. Blood 82 (10 Suppl. 1). 1993. 155A. ISSN: 0006–4571).

Merck Index 11th edition, 1989, #1020.

P. Fernandez, et al., Proc. Natl. Acad. Sci. USA, vol. 91, pp. 8641–8645, "Expression of a Specific Marker of Avian Programmed Cell Death in Both Apoptosis and Necrosis", Aug. 1994.

J. F. R. Kerr, et al. "Apoptosis: A Basic Biological Phenomenon with Wide–Ranging Implications in Tissue Kinetics", British Journal of Cancer, No. 26, 1972, pp. 239–257.

Gerard I. Evan, et al. "Induction of Apoptosis in Fibroblasts by C–MYC Protein", Cell , vol. 69, Apr. 3, 1992, pp. 119–128.

A. R. Clarke, et al., "Thymocyte Apoptosis Induced by p53–Dependent and Independent Pathways", Nature, vol. 362, Apr. 29, 1993, pp. 849–852.

Reid P. Bissonnette, et al., "Apoptotic Cell Death Induced by C–MYC is Inhibited by BCL–2", Nature, vol. 359, Oct. 8, 1992, pp. 552–554.

Abdallah Fanidi, et al., "Cooperative Interaction Between C–MYC and BCL–2 Proto–Oncogenes", Nature, vol. 359, Oct. 8, 1992, pp. 554–556.

Craig B. Thompson "Apoptosis in the Pathogenesis and Treatment of Disease", Science, vol. 267, Mar. 10, 1995, pp. 1456–1462.

Maj–Lis Smith, et al. "Models for Studying Long–Term Recovery Following Forebrain Ischemia in the Rat. 2. A 2–Vessel Occlusion Model", Acta Neurol Scand, No. 69, 1984, pp. 385–401.

Yael Gavrieli, et al. "Identification of Programmed Cell Death in Situ Via Specific Labeling of Nuclear DNA Fragmentation", The Journal of Cell Biology, vol. 119, No. 3, Nov. 1992, pp. 493–501.

Yuriko Tanaka et al, "Studies on the mechanism of activation of fibrinogen by thrombin or snake venom (Defibrase)", Blood & Vessel, vol. 11, pp. 30–34, 1980.

*Primary Examiner*—Jose' G. Dees
*Assistant Examiner*—Sabiha Qazi
*Attorney, Agent, or Firm*—Oblon, Spivak, McClelland, Maier & Neustadt, P.C.

[57] ABSTRACT

A pharmaceutical composition for prophylaxis and/or treatment of apoptosis-related diseases which comprises as an effective ingredient batroxobin.

6 Claims, No Drawings

METHODS FOR THE TREATMENT OF APOPTOSIS-RELATED DISEASES BY BATROXOBIN

FIELD OF THE INVENTION

This invention relates to a pharmaceutical composition for prophylaxis and/or treatment of apoptosis-related disease which comprises as an effective ingredient batroxobin.

BACKGROUND OF THE INVENTION

Apoptosis is one of the courses or manners of cell death proposed by Kerr, Wyllie, Currie et al. (see Brit. J. Cancer, 26, 239 (1972)). In embryology, there has been known cell death which occurs infallibly at a certain stage of embryogenesis at a certain place. This is also called "programmed cell death" to mean that it occurs according to the program of embryogenesis. Accordingly, it is morphologically differentiated from "necrosis" which is the course wherein necessary cells are injured to death. Morphological features of apoptosis include lack of contact with neighboring cells, concentration of cytoplasm, chromatin condensation and nucleus condensation which relate to endonuclease activity, and nucleus segmentation. Further, there are also observed disappearance of microvilli on the cell surface and planing of the cell surface (membrane blebbing). Moreover, fragmentation of DNA by endonuclease activity is also observed and cells form cellular fragments called apoptotic body, the resultant apoptotic body is rapidly and phagocytotically degraded by neighboring cells and macrophages. As a result, it is believed that apoptosis occurs.

It has been known that living bodies keep homeostasis by balancing cell growth with cell death. In the past, regulation of cell growth has been studied well but regulation of cell death has hardly been known. It has been known that apoptosis is induced by the lack of biologically active substances such as nerve growth factor (NGF) and colony stimulating factor (CSF), apoptosis inducing factor such as tumor necrosis factor (TNF), lymphotoxin, and gene products such as c-myc and p-53 (see Cell, 69, 119 (1992); Nature, 362,849 (1993)). It has also been known that apoptosis is inhibited by apoptosis inhibiting factor such as bcl-2 (see Nature, 359, 552 (1992); Nature, 359, 554 (1992)).

Recently, it has been recognized that apoptosis has important relation to various diseases and many trials have been made to induce or regulate cell apoptosis so as to diagnose, prevent and treat these diseases, to which attention has been drawn (see Science, 267,1456 (1995)).

Further, attention has also been drawn to the relation of apoptosis with hippocampal tardive nerve cell death in postischemic nerve cell death. Namely, when both side carotid arteries of Mongolian gerbil or rat are occluded for a short time (e.g., about 10 minutes) and then recanalized, cell death is observed in the both hippocampal CA1 region after two days (48 hours) and the cells are reduced after four days (96 hours) and vacuole is observed in dendrite, and disappear after one week.

The brain is a tissue in which oxygen consumption are highest in all the tissues and a place where a large amount of energy is consumed. Accordingly, the brain is weak against ischemia and is liable to undergo function disorder. Nerve cell death is markedly observed during embryogenesis and the cells constantly die after they are born. It is believed that about 100,000 nerve cells in human cerebral cortex will die a day. Nerve cells cannot regenerate. Accordingly, if the cells die to excess due to certain damage, function disorder will occur. Particularly, nerve cell death caused by ischemia, drugs, stress, or viruses is problematic. It becomes therefore much more important to elucidate the mechanism of the cell death so as to develop agents or methods for the treatment of neuronosis such as cerebral ischemia disorder or neuropathy due to AIDS, or to obtain a key to understand the long viability of the nerve cells.

Attention has also been drawn to the relation of apoptosis with neuro degenerative diseases such as Alzheimer's disease or Parkinson's disease, and it becomes more important to elucidate the mechanism of development of the diseases and to establish therapeutic methods or drugs for the treatment thereof.

SUMMARY OF THE INVENTION

An object of the present invention is to provide a pharmaceutical composition which regulates apoptosis so as to prevent and/or treat apoptosis-related diseases.

The inventors of the present invention has found that batroxobin is effective for prophylaxis and/or treatment of heart disease and cerebral disease in ischemia reperfusion and based on the finding has filed a patent application (U.S. Ser. No. 08/665,982 filed Jun. 19, 1996 claiming the priority of Japanese Patent Application No. Hei 7-161665). The invention is based on the finding that batroxobin inhibits "necrosis" which is a course in which cells are damaged to death. As described earlier, "apoptosis" and "necrosis" are morphologically different and the application is silent with respect to the relation between batroxobin and inhibition of apoptosis. The inventors of the present invention has studied the pharmacological action of batroxobin more in detail and found that batroxobin has the action to inhibit apoptosis and accomplished the present invention based on this finding.

Batroxobin used in the present invention is a thrombin-like enzyme derived from snake venom of Bothrops atrox moojeni and examples of commercially available formulations of the enzyme include "batroxobin formulation" manufactured by Tobishi Pharmaceutical Co., Ltd.

The pharmaceutical composition for prophylaxis and/or treatment of apoptosis-related diseases of the present invention inhibits apoptosis and can be used as a drug for prophylaxis and/or treatment of apoptosis-related diseases. Examples of the apoptosis-related diseases include ischemic disease (excluding reperfusion injury), neuro degenerative disease, peripheral nerve damage, apalstic anemia, liver damage and HIV infection. Examples of the ischemic diseases include heart disease such as cardiac infarction, cardiac angina, congestive heart failure and arrhythmia, and cerebrovascular diseases such as cerebral stroke, subarachnoidal hemorrhage, cerebral infarction, and cerebral thrombosis. Examples of the neuro degenerative diseases include Alzheimer's disease, Parkinson's disease, amyotrophic lateral sclerosis, pigmented retinitis, and cerebelli degeneration.

Batroxobin formulation (a thrombin-like enzyme derived from snake venom of Bothrops atrox moojeni)(1 ml) contains the following components.

| | |
|---|---|
| batroxobin (effective ingredient) | 10 BU |
| chlorobutanol (preservative) | 3 mg |
| gelatin hydrolysate (stabilizer) | 0.1 mg |
| sodium chloride (isotonizing agent) | 9 mg |
| distilled water for injection | to 1 ml |

Dosage of batroxobin in the present invention depends on the conditions and typically 1 to 20 batroxobin units (Batroxobin Unit, abbreviated as BU) per day per one time for human adult although it may vary depending on the conditions. The batroxobin formulation can suitably diluted and administered by intravenous drip infusion, intravenous injection or intraarterial injection. The batroxobin unit described herein is a unit representing an enzymatic activity of batroxobin and such an activity that the coagulation of plasma is taken place in 19.0±0.2 seconds when 0.1 ml of a batroxobin solution is added to 0.3 ml of standard human plasma containing citric acid at a temperature of 37° C. is defined as 2 BU.

Acute toxicity test for batroxobin was conducted by intravenous administration to mice, rats, rabbits and dogs. The resulted $LD_{50}$ values (BU/kg) were as follows:

| kinds of animal | $LD_{50}$ value (BU/kg) |
|---|---|
| mice (ddY strain) | 192 to 210 |
| rats (Wistar strain) | 105 to 110 |
| rabbits (NW species) | >300 |
| dogs (hybrid) | 190 to 208 |

The present invention will be specifically described with reference to Examples to which the present invention is not limited.

EXAMPLES

Apoptosis inhibitory effect of batroxobin in cerebral ischemia reperfusion injury model of rats method of experiment Fifty one male Wister rats weighing 250 to 300 g were used and divided into four groups: a control group (no treatment) of 6 rats, a pseudo-operating group of 9 rats, an ischemia control group of 18 rats and a batroxobin administering group of 18 rats. According to the Smith et al method (see Acta. Neurol. Scand, 69, 385 (1984)), common carotid arteries at both sides were occluded and average arterial blood pressure was maintained to 50 mmHg by bloodletting. After the common carotid arteries were occluded for ten minutes, 2 ml of physiological saline was administered to the ischemia control group and reperfusion was conducted. After 24, 48 and 96 hours, the rats were sacrificed by decapitation. To the batroxobin administering group, 2 ml of batroxobin solution in physiological saline was intravenously administered in the amount of 1.6 BU/kg. To the pseudo-operating group, the same procedures as in the ischemia group were conducted except that the occlusion of common carotid arteries and bloodletting were not conducted. To the control (no treatment) group, no treatment was conducted but the rats were directly sacrificed by decapitation.

Cell apoptosis was observed using "In situ cell death detection kit AP" (available from Boehringer Mannheim). Namely, frozen tissue section was fixed by 4% paraformaldehyde (available from Sigma), washed three times with PBS (phosphate buffered saline) and brought into contact with a TUNEL (TdT using nick end labeling) reaction mixture to label a DNA chain degradation product. The mixture was then allowed to stand at 37° C. for 45 minutes, washed with PBS, to which converter-AP was added and the mixture was treated at 37° C. for 60 minutes. In conventional manners, dehydration, clearing and mounting were conducted to observe apoptosis under light microscope. Chromatin of apoptosis cells was condensed in the form of meniscus around nuclear membrane, and purple-blue apoptotic body was observed. Apoptosis positive cells were observed and the number of the cells per one mm length was counted under light microscope (magnification of 400).

Statistical analysis was conducted according to Student's t-test and the results are expressed by average±standard deviation.

Results

In the control group (no treatment) and the pseudo-operating group, apoptotic body was not observed. In the ischemia control group, apoptosis positive cells were observed in the hippocampal CA1 region 24 hours after reperfusion. Chromatin of the cells were condensed in the nucleus in the form of typical meniscus and the existence of apoptotic body was recognized. With the time course after reperfusion, the number of apoptosis positive cells increased and reached the maximum after 96 hours. In the batroxobin administering group, apoptotic body was not observed 24 hours after reperfusion. The existence of apoptotic body was recognized 48 hours and 96 hours after reperfusion, but the number of apoptosis positive cells were markedly decreased as compared with the ischemia control group (see Table 1).

As explained above, batroxobin shows remarkable inhibitory action against apoptosis.

TABLE 1

Inhibitory action of batroxobin against apoptosis in the hippocampal CA1 region of rats (the number of apoptosis positive cells per one mm length)

| Group | Number of rats | Reperfusion time (hours) | | |
|---|---|---|---|---|
| | | 24 | 48 | 96 |
| no treatment | 6 | 0 | 0 | 0 |
| pseudo-operating | 9 | 0 | 0 | 0 |
| ischemia control | 18 | 2.83 ± 1.47 | 7.33 ± 2.75 | 26.17 ± 4.83 |
| batroxobin administering | 18 | 0** | 2.50 ± 1.05** | 6.67 ± 1.75** |

**: Comparison with the pseudo-operating group, $p < 0.01$

The pharmaceutical composition of the present invention for prophylaxis and/or treatment of apoptosis-related disease which comprises batroxobin shows the inhibitory action against apoptosis and is effective as an agent for prophylaxis and/or treatment of apoptosis-related diseases.

What is claimed is:

1. A method of inhibiting apoptosis, comprising administering an effective amount of batroxobin to a subject in need thereof, wherein the subject in need thereof is suffering from a disease selected from the group consisting of ischemic disease (excluding reperfusion injury), neuro degenerative disease, peripheral nerve injury, a plastic anemia, liver damage, and HIV infection.

2. The method of claim 1, wherein the subject in need thereof is suffering from neuro degenerative disease.

3. The method of claim 1, wherein the subject in need thereof is suffering from peripheral nerve injury.

4. The method of claim 1, wherein the subject in need thereof is suffering from aplastic anemia.

5. The method of claim 1, wherein the subject in need thereof is suffering from HIV infection.

6. The method of claim 1, wherein the batroxobin is administered in the form of a pharmaceutically acceptable composition.

* * * * *